(12) United States Patent
Birke et al.

(10) Patent No.: US 6,368,389 B1
(45) Date of Patent: Apr. 9, 2002

(54) METHOD FOR SEPARATING VAPOROUS PHTHALIC ACID ANHYDRIDE FROM A GAS STREAM

(75) Inventors: Gerhard Birke, Frankfurt/Main; Martin Hirsch, Friedrichsdorf; Volker Franz, Frankfurt/Main, all of (DE)

(73) Assignee: Metallgesellschaft Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/554,925

(22) PCT Filed: Feb. 23, 1999

(86) PCT No.: PCT/EP99/01158

§ 371 Date: May 18, 2000

§ 102(e) Date: May 18, 2000

(87) PCT Pub. No.: WO99/48583

PCT Pub. Date: Sep. 30, 1999

(30) Foreign Application Priority Data

Mar. 26, 1998 (DE) .......................... 198 13 286

(51) Int. Cl.⁷ .............................. B01D 7/02; B01D 53/00
(52) U.S. Cl. ............................ 95/275; 95/276; 95/290; 96/373; 55/282.5; 55/338.1; 55/340; 55/474
(58) Field of Search .......................... 95/275, 276, 290; 96/372, 377, 373; 55/282.5, 338, 338.1, 340, 418.1, 428.1, 474, 476, 490.1, 512; 165/104.18

(56) References Cited

U.S. PATENT DOCUMENTS

| | | | |
|---|---|---|---|
| 3,791,110 A | | 2/1974 | Klein et al. |
| 5,110,323 A | * | 5/1992 | Soni ............................ 95/275 |
| 5,205,350 A | * | 4/1993 | Hirsch et al. .......... 165/107.18 |
| 5,455,290 A | * | 10/1995 | Kitagawa et al. ........... 523/443 |
| 5,464,597 A | * | 11/1995 | Tang .......................... 423/210 |
| 5,505,907 A | * | 4/1996 | Hiltunen et al. ............ 422/146 |
| 5,567,228 A | * | 10/1996 | Adulally ...................... 55/340 |
| 6,109,342 A | * | 8/2000 | Klaren ................... 165/104.16 |

FOREIGN PATENT DOCUMENTS

| | | |
|---|---|---|
| EP | 0 467 441 | 1/1992 |
| GB | 988084 | 4/1965 |

\* cited by examiner

*Primary Examiner*—Duane Smith
*Assistant Examiner*—Jason M. Greene
(74) *Attorney, Agent, or Firm*—Herbert Dueno

(57) ABSTRACT

Phthalic acid anhydride is recovered from a gas stream containing phthalic acid anhydride vapors by passing the gas stream upwardly through a vertical tube so that the gases expand at the orifice at the upper end of the tube and mix with granules entrained above the tube by fluidizing gas of a fluidized bed of phthalic acid anhydride granules around the tube. The tube, kept free from phthalic acid anhydride granules and the fluidized bed, is indirectly cooled.

8 Claims, 1 Drawing Sheet

METHOD FOR SEPARATING VAPOROUS PHTHALIC ACID ANHYDRIDE FROM A GAS STREAM

CROSS REFERENCE TO RELATED APPLICATIONS

This application is a national stage of PCT/EP99/01158 filed Feb. 23, 1999 and based, in turn, upon German national application 198 13 286.7 filed Mar. 26, 1998 under the International Convention.

FILED OF THE INVENTION

The present invention relates to a process for separating or recovering phthalic acid anhydride (PA) contained in the form of vapor in a gas stream by cooling the gas stream and solidifying the PA in a cooler which contains a fluidized bed that consists of granules containing PA, where the fluidized bed is cooled indirectly.

BACKGROUND OF THE INVENTION

Such a process is known from GB-A-988084. In accordance with this process, the gas stream containing PA is introduced into the lower portion of a cooled fluidized bed. However, the gas is forced through the fluidized bed largely in the form of bubbles which exhibit a very stable behavior. The gas bubbles prevent an intensive heat transfer between the PA vapor contained in the bubbles and the relatively cold solid particles of the fluidized bed. The cooling of the PA vapor is therefore insufficient, and experience has shown that one can only achieve a condensation of nor more than 50% of the PA vapor in the fluidized bed.

SUMMARY OF THE INVENTION

It is the object underlying the invention to intensively cool the gas stream containing vaporous PA by means of an indirectly cooled fluidized bed, so that the PA is separated from the gas stream with a high efficiency. In accordance with the invention this is achieved in that the gas stream containing vaporous PA is passed in an upward direction through a vertical tube disposed in the lower portion of the cooler, that the vertical tube has an upper orifice, that the tube and its orifice are surrounded by the indirectly cooled fluidized bed, whose temperature lies in the range from 20 to 90° C. and to which fluidizing gas is supplied from the bottom, where the suspension density of the fluidized bed lies in the range from 300 to 700 kg/m$^3$, that the inner portion of the tube has no fluidized bed, that from the fluidized bed through the orifice of the vertical tube granules of the fluidized bed are constantly introduced into the gas stream containing vaporous PA and are supplied by the gas stream to a settling space disposed in the cooler upstream of the tube and above the fluidized bed, where vaporous PA contained in the gas stream is cooled and solidified, and where solidified PA at least partly drops from the settling space onto the fluidized bed, that gas is discharged from the settling space and from the cooler, and that granules containing PA are withdrawn from the fluidized bed.

By means of the inventive process, more than 90% of the introduced PA vapor is cooled and solidified in the cooler. Usually, 10 to 50 kg solids per Nm$^3$ gas will be introduced from the fluidized bed in the vicinity of the orifice of the vertical tube into the gas stream containing PA. The settling space and also the area directly above the orifice of the vertical tube is free from a fluidized bed. There are only relatively small amounts of solids, so that gas bubbles cannot be formed there as they are, however, inevitable in a fluidized bed.

Advantageously, the granules of the fluidized bed comprise at least 80 wt-% grain sizes of not more than 1 mm, when no auxiliary granules are employed. The relatively fine-grained granules have a good flowability and can be indirectly cooled in the fluidized bed with high heat transfer coefficients.

For fluidizing the fluidized bed various gases may be used. Expediently, there is used at least partly deducted gas withdrawn from the cooler, or air, or a mixture of these two gases.

The gas stream containing the vaporous PA usually comes from a reactor for catalytically producing PA from orthoxylene or naphthalene with air. The gas stream containing vaporous PA, which is produced in this known way, can first of all be cooled indirectly in one or several stages in a waste heat boiler before it is introduced into the vertical tube for final cooling. A precooling without condensation and without producing solid PA may be advantageous when it is desired to reduce the thermal load in the final cooling.

A cooler of the type used in the inventive process for solidifying the PA vapor in described in EP-B-0467441. This cooler is in particular provided for cooling an exhaust gas from the process of smelting lead ore, where the purification of gas chiefly meets the requirements of environmental protection. It has now been discovered that the basically known cooler is able to solidify relatively large amounts of PA, which are supplied in the form of vapor.

For producing the fluidized bed in the cooler, which surrounds the vertical tube, one can omit auxiliary granules or employ such auxiliary granules, e.g. sand with grain sizes of about 0.05 to 1 mm. In the cooled fluidized bed, PA in condensed on the auxiliary granules and is withdrawn together with the same. Outside the fluidized bed the crude PA is separated from the auxiliary granules, e.g. by melting it off, and the auxiliary granules can be recirculated to the fluidized bed. When no auxiliary granules are employed, this separation step is omitted.

BRIEF DESCRIPTION OF THE DRAWING

Embodiments of the process will be explained with reference to the drawing. The drawing represents a flow diagram of the process.

In the tubular reactor 1, PA is catalytically produced in a manner known per se at temperatures from about 300 to 500° C. from a mixture of naphthalene or orthoxylene and air, which is supplied via line 2. The gas stream containing-vaporous PA, which is obtained as a product of the reaction in the reactor 1, flows via line 3 to a waste heat boiler 4, in which a first cooling is effected. PA is not yet condensed. With temperatures of usually 150 to 250° C., the gas stream containing PA then flows through lines 5 and 5*b*, through the opened valve 6 and line 7 to the final cooler 9. In this process variant, the valve 8 is closed.

Figure 1:
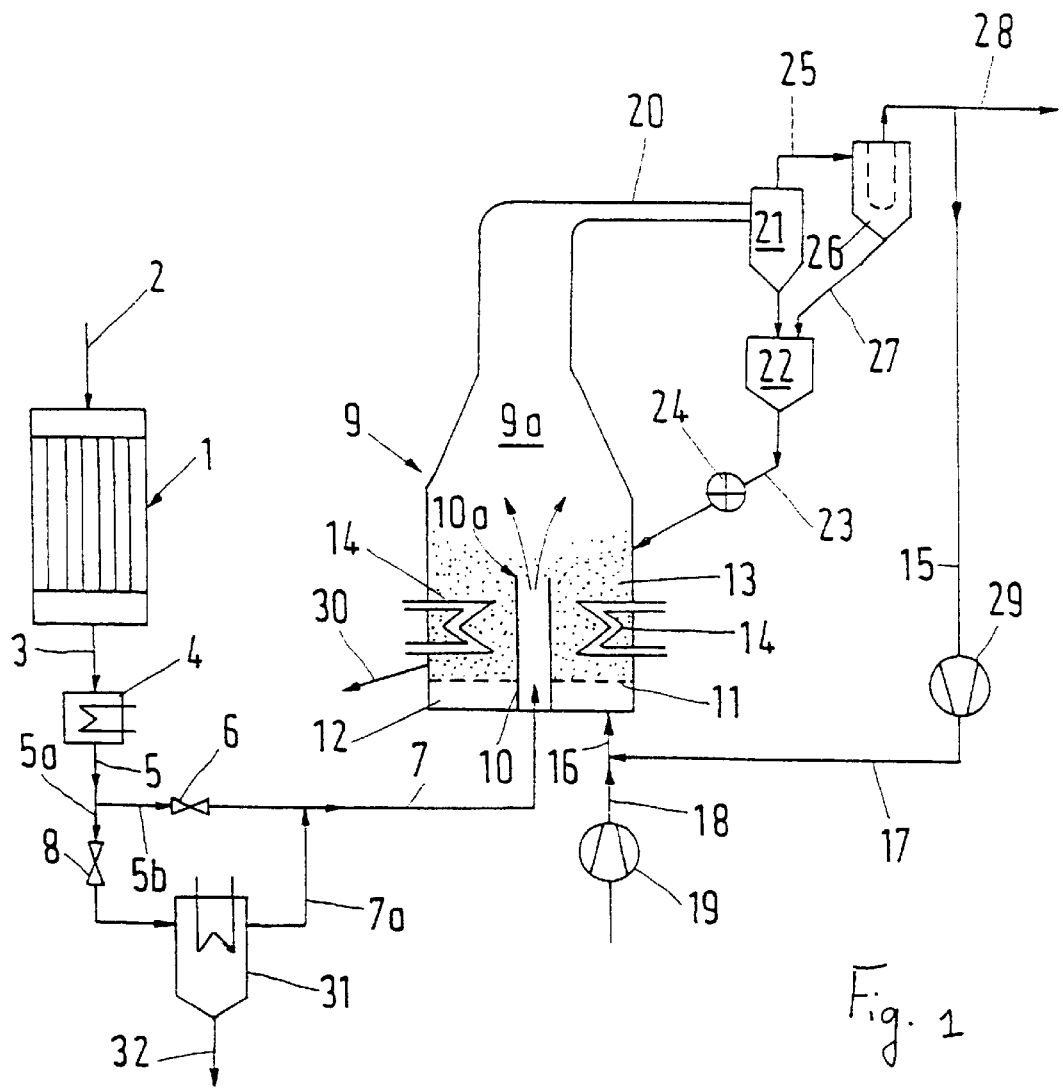

In its lower central portion, the cooler 9 comprises a vertical tube 10, a gas distributor 11 and below the same a distribution chamber 12 for fluidizing gas. The annular space surrounding the tube 10 is provided with cooling elements 14, through which a cooling fluid flows for dissipating heat. At the cooling fluid, water or oil may be used. In the annular space of the cooler 9 above the gas distributor 11 there is provided a fluidized bed 13 of granules containing PA. The fluidized bed extends a little beyond (above) the upper orifice 10*a* of the tube 10. At least 80 wt-% of the granules of the fluidized bed have grain sizes in the range of not more than 1 mm. Fluidizing gas, which flows upwards through the gas distributor 11, is first of all delivered through line 16 into the distribution chamber 12. This fluidizing gas may either be recirculated gas from line 17 or air from line 18, which is sucked in by the blower 19, or a mixture of air and recirculated gas.

In the final cooler 9, the empty-tube velocity of the fluidizing gas in the fluidized bed 13 usually lies in the range from 0.1 to 0.6 m/s. The gas velocities in the tube 10 approximately lie in the range from 20 to 50 m/s, and in the settling space 9a, which is disposed above the orifice 10a, the effective gas velocity is about 2 to 3 m/s. The volume of the fluidizing gas is 10 to 30% and mostly 15 to 25% of the volume of the gas stream in line 7. The suspension density in the fluidized bed 13 lies in the range from 300 to 700 kg/m$^3$ and mostly 350 to 600 kg/m$^3$. The fluidized bed 13 ends just above the orifice 10a of the tube 10. Granules cooled in the fluidized bed 13 are mixed in this way with the gas steam leaving the tube 10, are delivered by the same upwards into the settling space 9a and thus ensure a rapid and intensive cooling of the gas and of the vaporous PA. The gas-solids suspension is blown into the settling space 9a, where the gas velocity quickly declines as a result of the expansion of the gas jet. The solids decrease in velocity and drop back into the fluidized bed 13. It may be expedient to provide the inner wall of the cooler 9 with cooling elements, also in the vicinity of the settling space 9a and above the same, such cooling elements have not been included in the drawing for simplification.

To provide sufficiently cooled granules in the fluidized bed 13, the temperatures thereof are usually maintained at 20 to 90° C. and preferably 50 to 80° C. As product, PA granules are withdrawn from the cooler 9 through line 30. These granules are usually supplied to a fine purification known per se, as it is described for instance in DE-D-3538911. When auxiliary granules are employed, e.g. sand, the grains thereof are enlarged by adhering PA in the cooled fluidized bed. These granules are withdrawn via line 30, and PA is separated from the auxiliary granules, e.g. by melting it off.

Gas which carries a certain amount of solids is withdrawn from the upper end of the cooler 9 through the passage and is first of all supplied to a cyclone separator 21. Separated solids are collected in the buffer vessel 22 and from there are delivered through line 23 and a metering member 24 back into the cooler 9. The gas leaving the separator 21 flows through line 25 to a filter 26, where separated solids are charged into the buffer vessel 22 through line 27. The filter 26 may for instance be a bag filter or an electrostatic precipitator. Dedusted gas escapes via line 28 and may wholly or in part be supplied to a not represented postcombustion. Usually, a partial stream of the deducted gas is branched off via line 15 and in recirculated as fluidizing gas through the blower 29 and line 17 to the cooler 9.

One process variant consists in that with valve 6 closed and valve 8 open the PA-containing gas coming from the waste heat boiler 4 La passed through a cooler 31, in which part of the PA is condensed and is withdrawn in liquid form via line 32. The remaining gas containing PA is then supplied through lines 7a and 7 to the final cooler 9.

EXAMPLE

There in employed a procedure corresponding to the drawing, where valve 6 is closed and valve 8 is open. The final cooler 9 has a total height of 10 m, a diameter in the vicinity of the fluidized bed 13 of 3 m and a height between the distributor 11 and the upper orifice 10a of the tube 10 of 2 m. In the tube 10, which has a diameter of 0.7 m, the van velocity in 40 m/sec, the empty-tube velocity of the fluidizing gas in the annular space 13 is 0.3 m/sec. The fluidized bed 13 has a suspension density of 450 kg/m$^3$, the grain sizes of the PA granules are below 1 mm, and the average $d_{50}$ is 0.3 mm. No auxiliary granules are employed in the cooler 9.

Per hour, 3900 kg orthoxylene are reacted with 51600 kg air in the tubular reactor 1. The pressures lie between 1 and 1.5 bar, the data indicated below have been calculated in part.

The games mentioned in the Table are mixtures containing $O_2$, $N_2$, $CO_2$ and $H_2O$.

| Line | 3 | 7 | 30 |
| --- | --- | --- | --- |
| PA (kg/h) | 4283 | 2364 | 2324 |
| Orthoxylene (kg/h) | 0.5 | 0.5 | — |
| Byproducts (kg/h) | 245 | 243 | 2 |
| Gases (kg/h) | 50990 | 50980 | 1 |
| Temperatures (° C.) | 370 | 137 | 65 |

Per hour, 2000 m$^3$ air are supplied via line 18, and 6000 m$^3$ steam-containing gas with a temperature of 100° C. flows in line 17. Through line 28, 50300 m$^3$ of steam-containing gas are withdrawn from the process.

What is claimed is:
1. A method of recovering phthalic acid anhydride from a gas stream containing phthalic acid anhydride as a vapor, comprising the steps of:
(a) continuously passing said gas stream containing phthalic acid anhydride as a vapor upwardly through a vertical tube having a discharge orifice at an upper end of said vertical tube;
(b) fluidizing a bed of granules containing phthalic acid anhydride around said tube by passing a fluidizing gas upwardly through said bed and inducing granules from said bed to migrate above said discharge orifice and to mix with the gas stream containing phthalic acid anhydride an a vapor an said gas stream emerges from said orifice;
(c) cooling said gas stream at least in part by expanding said gas stream into a space above said bed and said orifice wherein said gas stream mixes continuously with said granules, whereby phthalic acid anhydride deposits on said granules and said granules fall back from said space into said bed;
(d) indirectly cooling said bed to a temperature in a range of 20° C. to 90° C. by passing a cooling fluid through cooling elements in contact therewith;
(e) maintaining a suspension density of the granules in said bed of 300 to 700 kg/m$^3$ and an interior of said tube free from said granules;
(f) continuously withdrawing gas from said space above said bed and said orifice; and
(g) withdrawing granules containing phthalic acid anhydride from said bed.
2. The method defined in claim 1 wherein, at said orifice, 10 to 50 kg of solids per standard m$^3$ are introduced into said gas stream.
3. The method defined in claim 1 wherein said gas stream is cooled in at least one cooling stage before being introduced into said vertical tube.
4. The method defined in claim 1 wherein at least part of the gas withdrawn from said space in step (f) is introduced into said bed in step (b) as a fluidizing gas.

5. The method defined in claim 1 which comprises controlling the particle size of said granules in said bed so that at least 80% by weight thereof has a particle size of not more than 1 mm.

6. The method defined in claim 1 wherein air is introduced into said fluidized bed as a fluidizing gas.

7. The method defined in claim 1 wherein said gas stream is passed first into an indirect heat exchanger in which liquid phthalic acid anhydride is formed and is then passed into said tube, said method further comprising the step of withdrawing liquid phthalic acid anhydride from said indirect heat exchanger.

8. The method defined in claim 1, further comprising the step of introducing auxiliary granules into said fluidized bed.

* * * * *